US00PP24271P3

(12) United States Plant Patent
Wu et al.

(10) Patent No.: US PP24,271 P3
(45) Date of Patent: Feb. 25, 2014

(54) 'LATITUDE 36 TURF BERMUDAGRASS'

(50) Latin Name: ***Cynodon dactylon* (L.) Pers. *xc. transvaalensis* Burtt-Davy**
Varietal Denomination: Latitude 36 Turf Bermudagrass

(75) Inventors: Yanqi Wu, Stillwater, OK (US); Dennis Loren Martin, Stillwater, OK (US); Charles M. Taliaferro, Stillwater, OK (US); Jeffrey A. Anderson, Stillwater, OK (US); Justin Q. Moss, Perkins, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 52 days.

(21) Appl. No.: 13/317,967

(22) Filed: Oct. 31, 2011

(65) Prior Publication Data

US 2012/0304349 P1 Nov. 29, 2012

Related U.S. Application Data

(60) Provisional application No. 61/456,109, filed on Nov. 1, 2010.

(51) Int. Cl.
*A01H 5/00* (2006.01)

(52) U.S. Cl.
USPC ..... Plt./389

(58) Field of Classification Search
USPC ..... Plt./389
See application file for complete search history.

(56) References Cited

PUBLICATIONS

Wu et al. Turfgrass and Environmental Research Online vol. 8, No. 16 Aug. 15, 2009.*
"Australian Patent Office PCT International Search Report; International Application PCT/US2011/001842", Dec. 12, 2011.
"Australian Patent Office PCT Written Opinion of the ISA, International Application PCT/US2011/001842", Dec. 12, 2011.
Wu, et al., "Turfgrass and Environmental Research Online", Aug. 15, 2009, vol. 8, No. 16, Published in: US.

* cited by examiner

*Primary Examiner* — Annette Para
(74) *Attorney, Agent, or Firm* — Fellers, Snider, Blankenship, Bailey & Tippens, P.C.

(57) ABSTRACT

'Latitude 36 Turf Bermudagrass' is a clonally propagated F I hybrid from a cross of *Cynodon dactylon* accession A 12198 (2n=4x=36)×*C. transvaalensis* OSU selection '2747' (2n=2x=18).

6 Drawing Sheets

SUMMARY OF THE INVENTION

A new turf bermudagrass cultivar, 'Latitude 36', is disclosed. Designated "Bermudagrass, *Cynodon dactylon* (L.) Pers. ×*c. transvaalensis* Burtt-Davy", the 'Latitude 36 Turf Bermudagrass' cultivar is also referred to herein by its experimental designation 'OKC 1119'.

DETAILED BOTANICAL DESCRIPTION

Description, Origin and History

Figure 1:
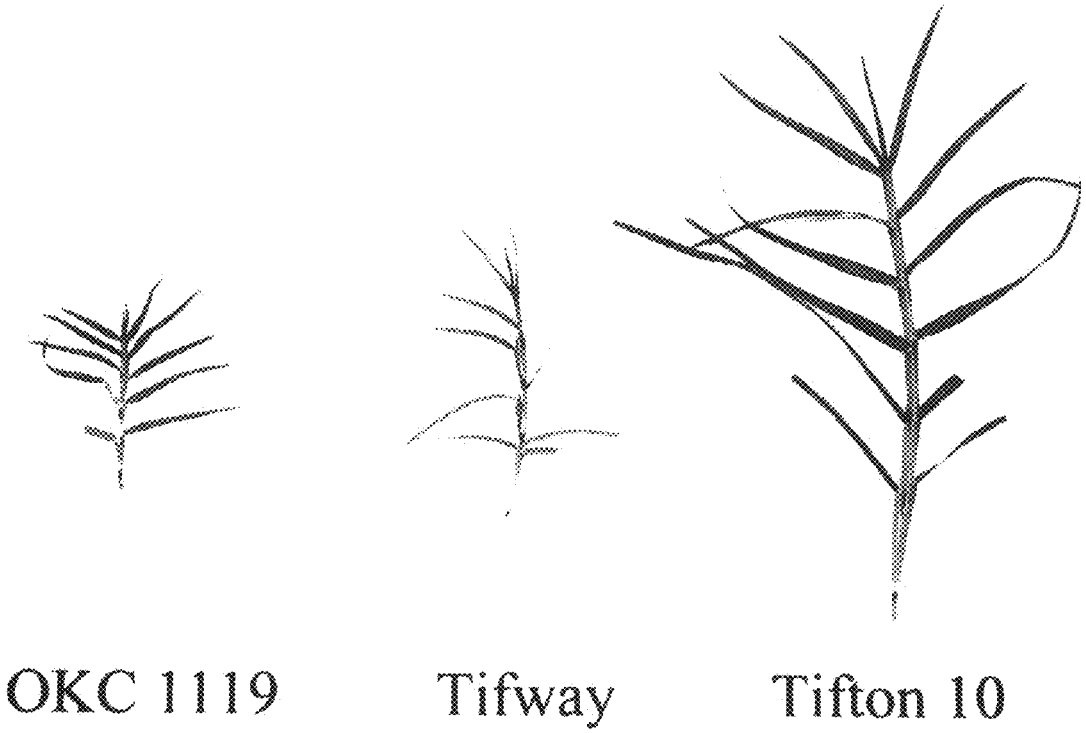
FIG. 1 is a comparison of 'Latitude 36 Turf Bermudagrass' (denoted as 'OKC 1119') to Tifway and Tifton 10.
Figure 2:
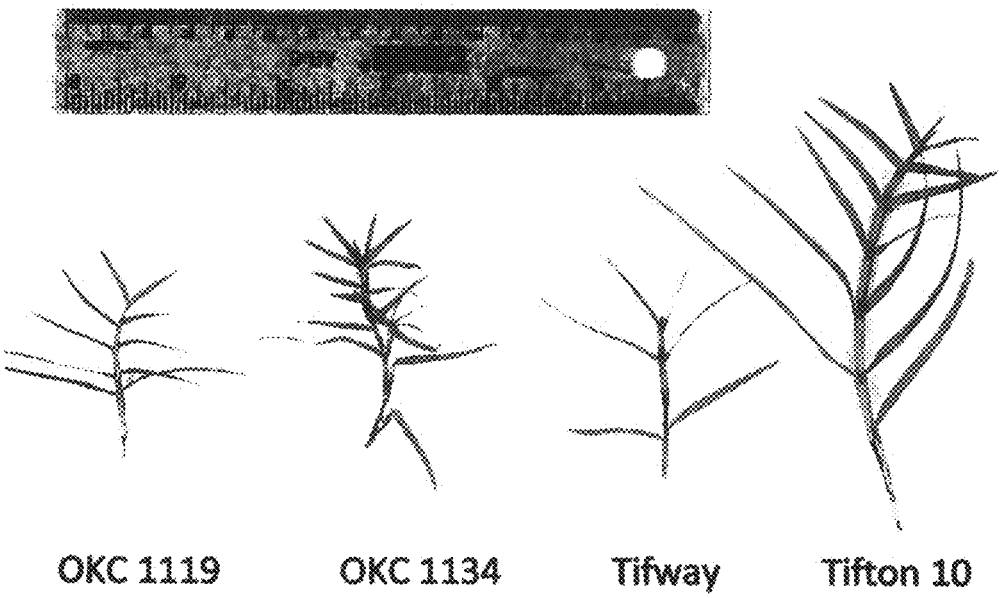
FIG. 2 is a comparison of 'Latitude 36 Turf Bermudagrass' (denoted as 'OKC 1119') to OKC 1134, Tifway, and Tifton 10.
Figure 3:
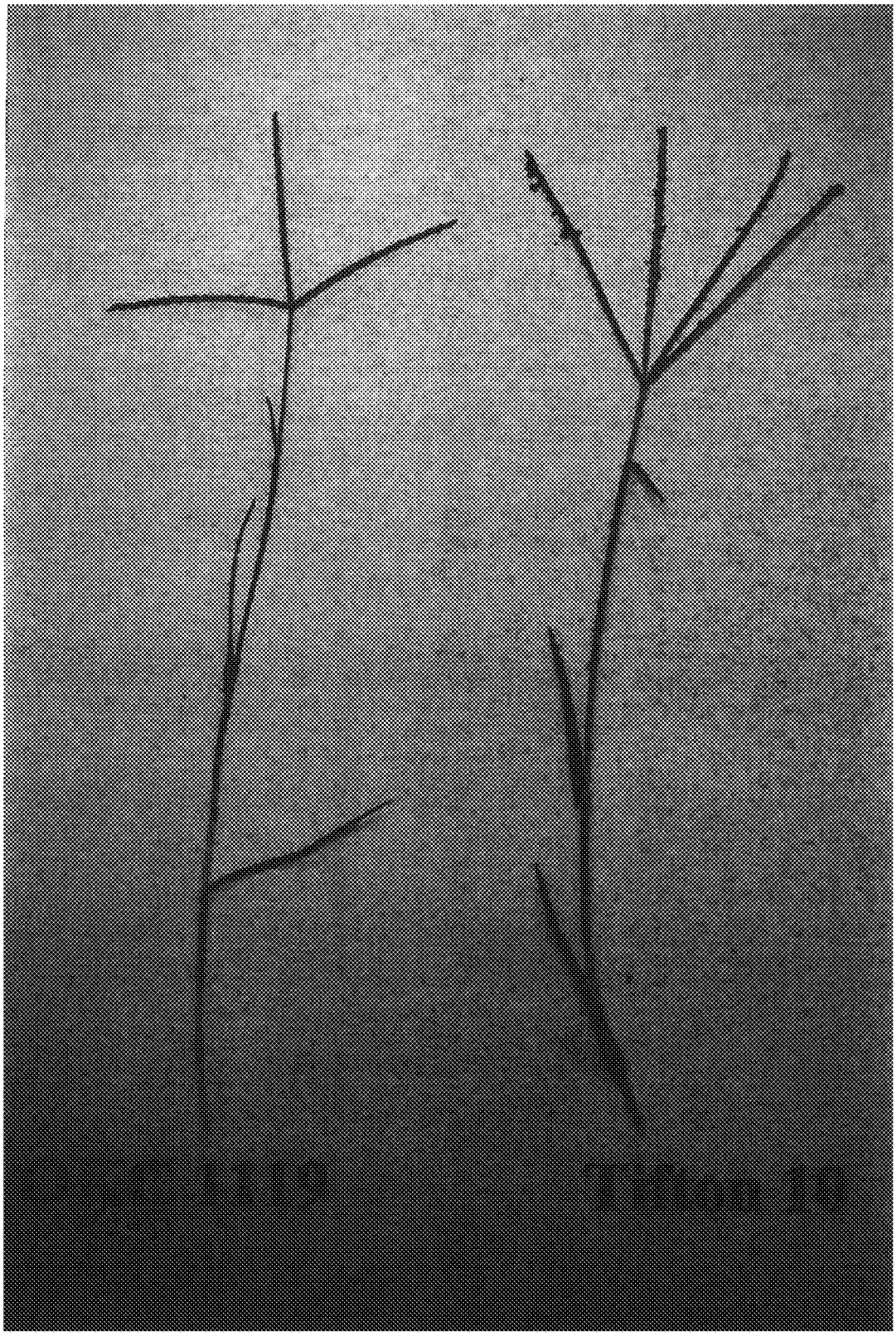
FIG. 3 is a photo of the inflorescense of 'Latitude 36 Turf Bermudagrass' (denoted as 'OKC 1119') and Tifton 10.
Figure 4:
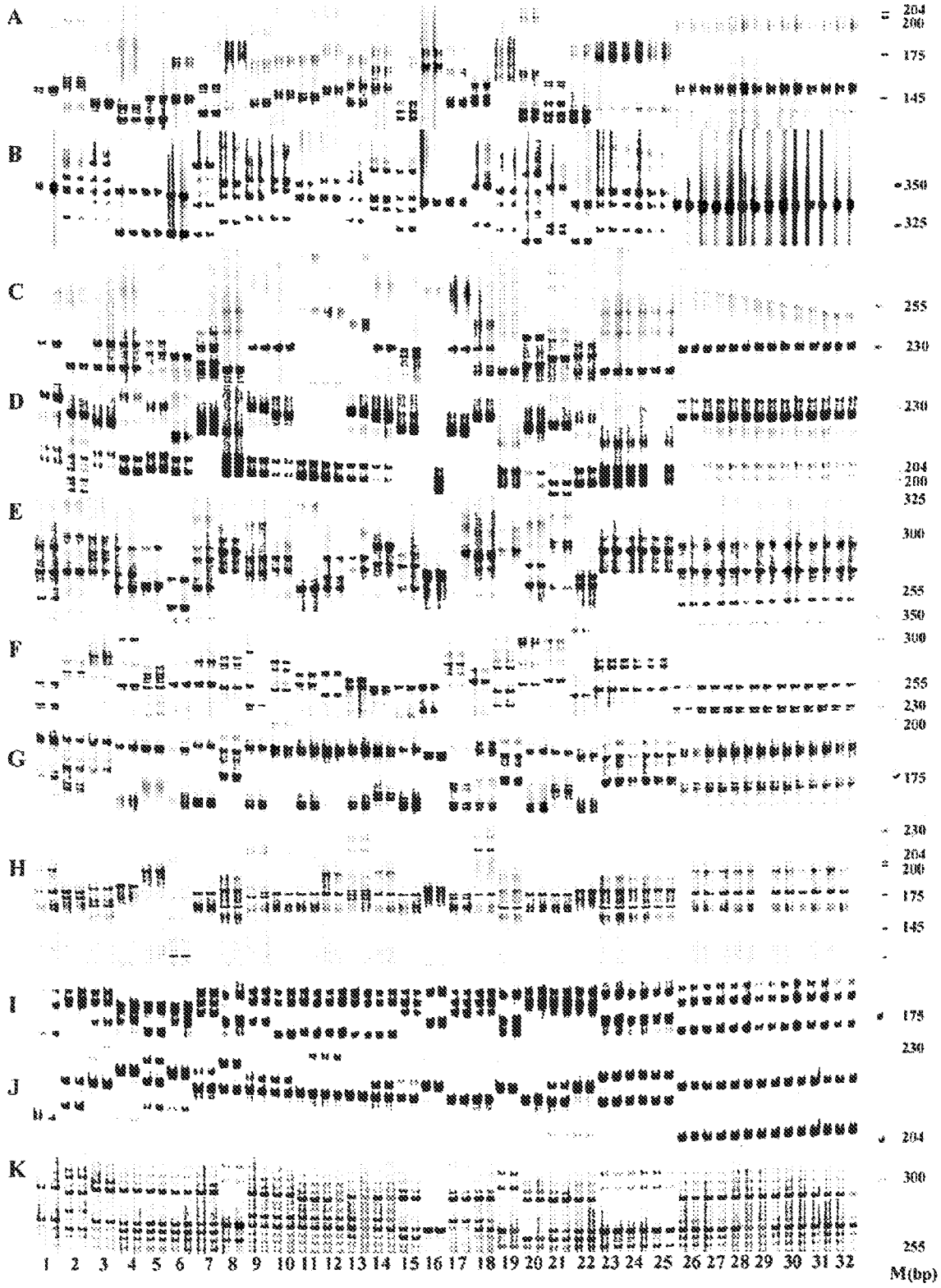
FIG. 4 is a diagram of DNA profiles of various turf bermudagrass cultivars.
Figure 5:
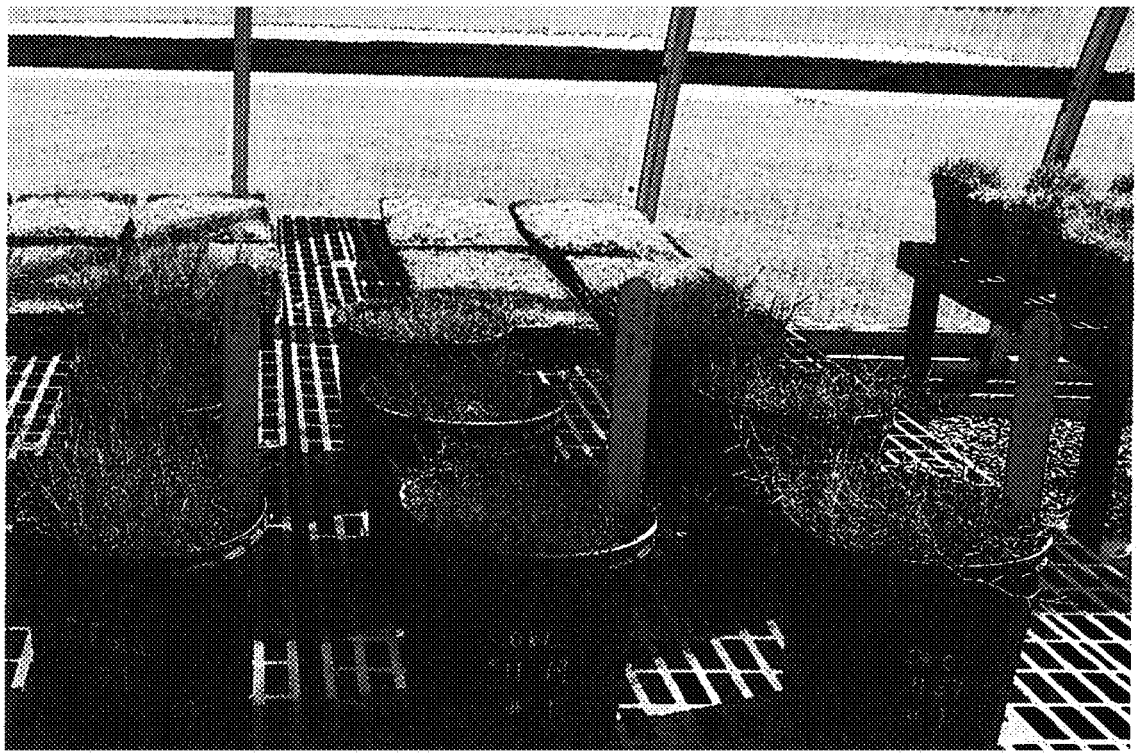
FIG. 5 is a comparison of 'Latitude 36 Turf Bermudagrass' (denoted as 'OKC 1119') to OKC 1134 and Tifway in a greenhouse.
Figure 6:
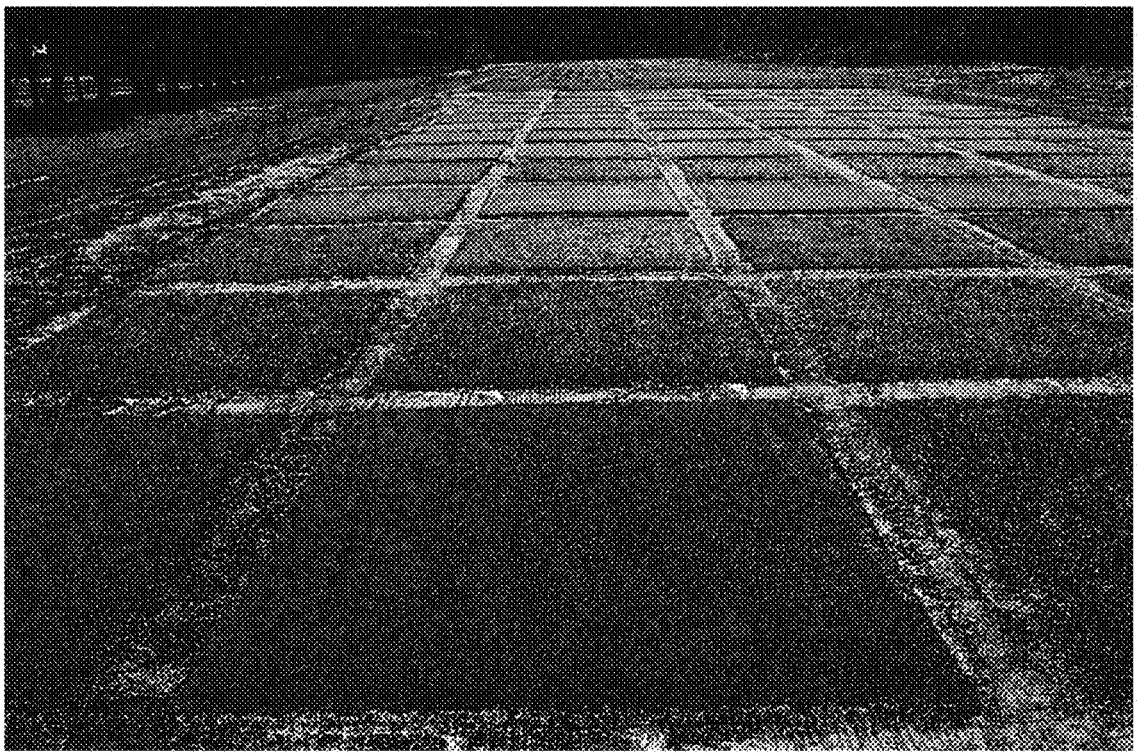
FIG. 6 is a patch of 'Latitude 36 Turf Bermudagrass' (denoted as 'OKC 1119') growing outdoors.

'Latitude 36 Turf Bermudagrass' is a clonally propagated F I hybrid from a cross of *Cynodon dactylon* accession A 12198 (2n=4x=36)×*C. transvaalensis* OSU selection '2747' (2n=2x=18). A12198 was collected in Beijing, PRC. *C. transvaalensis* 2747 was selected from a broad genetic base breeding population. Crossing of the two parent plants was achieved by planting clonal plants of each parent in close proximity in a small nursery isolated from other bermudagrass. Seed harvested in 1999 from plants of the respective parents in the crossing block was used to start 609 individual spaced plants in a screening nursery in May 2000 on the Agronomy Research Station EF A W farm. In fall 2001, 14 plants from the EF A W screening nursery were advanced to a second level two-replicate screening test on the Agronomy Research Station. The hybrid plant designated as OKC 11-19 'Latitude 36 Turf Bermudagrass' had A12198 as its maternal parent. In summer 2004, 'Latitude 36 Turf Bermudagrass' was included in a replicated mowing evaluation test at the Turf Research Center, Stillwater, Okla. This test was conducted under a golf course fairway management protocol and evaluated entries for many criteria influencing performance. 'Latitude 36 Turf Bermudagrass' was entered in the 2007 National Turfgrass Evaluation Program (NTEP) bermudagrass test.

'Latitude 36 Turf Bermudagrass' has 2n=3x=27 chromosomes, having presumably inherited 18 chromosomes from the A12198 *C. dactylon* parent and 9 chromosomes from the *C. transvaalensis* parent. It is sterile and must be vegetatively propagated. OSU SSR molecular marker DNA profiling experiments definitely indicated 'Latitude 36 Turf Bermudagrass' is a unique genotype, distinct from other commercial cultivars, and OKC 1134 and OKC 70-18 (Wang et al., 2010).

For mature plants grown in a greenhouse, 'Latitude 36 Turf Bermudagrass' had more narrow leaf blade width and shorter internode length relative to the commercial standard cultivars, Tifway and Tifton 10 (Table 1). Internode diameter of 'Latitude 36 Turf Bermudagrass' was similar to that of Tifway, and much less than that of Tifton 10 (Table 1). For plants grown in the field, the leaf blade width of 'Latitude 36 Turf Bermudagrass' was similar to that of Tifway and significantly less than that of Tifton 10 at two test locations (Table 2). The leaf blade length of field-grown 'Latitude 36 Turf Bermudagrass' plants was not significantly different from Tifway at the Cimarron Valley Research Station (CVRS) and greater than Tifway at the Agronomy Research Station (ARS) (Table 2). The leaf blade length of 'Latitude 36 Turf Bermudagrass' was greater than that of Tifton 10 at both test locations. Internode length of field-grown 'Latitude 36 Turf Bermudagrass' plants was not significantly different from that of Tifton 10 at the ARS, but significantly greater at the CVRS (Table 2). Internode length of 'Latitude 36 Turf Bermudagrass' was shorter than that of 'Tifway' at both test locations. Internode diameter of 'Latitude 36 Turf Bermudagrass' was less than that of Tifton 10 at both test locations, did not differ from that of Tifway at the ARS and was greater than that of Tifway at the CVRS (Table 2).

TABLE 1

Table 1. Measurements of leave blades and internodes of potted plants of Latitude 36, Tifway and Tifton 10 bermudagrasses, grown in a greenhouse at the Agronomy Research Station, Oklahoma State University. The data were collected in 2010 from three replications of each cultivar subsampled 10 times.

| Measured traits | Latitude 36 | Tifway | Tifton 10 | 5% LSD |
|---|---|---|---|---|
| $4^{th}$ leaf blade length (cm) * | 1.68 | 1.97 | 2.80 | 0.33 |
| $4^{th}$ leaf blade width (mm) | 1.48 | 1.83 | 2.72 | 0.12 |
| $2^{nd}$ internode length (cm) | 0.48 | 1.12 | 1.09 | 0.15 |
| $2^{nd}$ internode diameter (mm) | 0.58 | 0.56 | 1.01 | 0.07 |

*From shoot apex.

TABLE 2

Table 2. Measurements of leave blades and internodes of field-grown plants of Latitude 36, Tifway and Tifton 10 bermudagrasses. The field plots were established in 2010 and data were collected on 30 samples of three replications for each cultivar in 2011.

| Location | Measured traits | Latitude 36 | Tifway | Tifton 10 | 5% LSD |
|---|---|---|---|---|---|
| Agronomy Research Farm, Stillwater, OK | $4^{th}$ leaf blade length (cm) | 5.19 | 4.42 | 3.39 | 0.43 |
| | $4^{th}$ leaf blade width (mm) | 1.66 | 1.73 | 2.80 | 0.15 |
| | $2^{nd}$ internode length (cm) | 0.84 | 1.61 | 0.69 | 0.22 |
| | $2^{nd}$ internode diameter (mm) | 0.47 | 0.47 | 1.02 | 0.07 |
| Cimarron Valley Research Station, | $4^{th}$ leaf blade length (cm) | 3.87 | 3.94 | 3.07 | 0.48 |
| | $4^{th}$ leaf blade width (mm) | 1.68 | 1.78 | 2.64 | 0.16 |

TABLE 2-continued

Table 2. Measurements of leave blades and internodes of field-grown plants of Latitude 36, Tifway and Tifton 10 bermudagrasses. The field plots were established in 2010 and data were collected on 30 samples of three replications for each cultivar in 2011.

| Location | Measured traits | Latitude 36 | Tifway | Tifton 10 | 5% LSD |
|---|---|---|---|---|---|
| Perkins, OK | $2^{nd}$ internode length (cm) | 0.82 | 1.02 | 0.63 | 0.17 |
| | $2^{nd}$ internode diameter (mm) | 0.65 | 0.54 | 1.14 | 0.08 |

'Latitude 36 Turf Bermudagrass' DNA profiles are different from those of 30 commercial clonal bermudagrass cultivars and one experimental genotype as revealed by 11 simple sequence repeat (SSR) markers (FIG. 1) (Wang et al., 2010).

FIG. 1 illustrates DNA profiles of 32 vegetative turf bermudagrass cultivars amplified with 11 SSR primer pairs (PPs). The numbers at the bottom of the gel images: 1=Baby, 2=Celebration, 3=FloraTex, 4=Midfield, 5=Midlawn, 6=Midway, 7=MS-Choice, 8=MS-Price, 9=MS-Express, 10=OKC 70-18, 11=Latitude 36 ('Latitude 36 Turf Bermudagrass'), 12=NorthBridge (OKC 1134), 13=Patriot, 14=Premier, 15=Quickstand, 16=Sunturf, 17=Texturf 10, 18=Tifton 10, 19=TifGrand, 20=U-3-SIU, 21=Vamont, 22=Midiron, 23=TifSport, 24=Tifway, 25=Tifway II, 26=TifEagle, 27=Tifgreen, 28=Champion, 29=FloraDwarf, 30=Mini Verde, 31=MS-Supreme, 32=TifDwarf. Image A (labeled on the left side) was generated by SSR PP CDCA31-32, B by CDCA55-56, C by CDCA77-78, D by CDCA133-134, E by CDCA155-156, F by CDCA379-380, G by CDCA747-748, H by CDE89-90, I by CDE127-128, J by CDE215-216, and K by CDE375-376 (Wang et al., 2010. With permission from *Crop Science*).

Characteristics and Performance

'Latitude 36 Turf Bermudagrass' has been evaluated in several OSU experiments, and more comprehensively and extensively at 19 locations in the National Turfgrass Evaluation Program (NTEP) 2007 National Bermudagrass Test. Eight trial locations provided data for test year 2007, 16 locations for 2008, and all 19 locations for 2009 (see 2007 Progress Report NTEP No. 09-2; 2008 Progress Report NTEP No. 09-1; 2009 Progress Report NTEP No. 10-4, each incorporated herein by reference as if set out in its entirety, these may be found at: http://www.ntep.org/bg.htm). The major performance characteristics of 'Latitude 36 Turf Bermudagrass' are described as follows:

Turf quality: Turf quality of 'Latitude 36 Turf Bermudagrass' is very high as indicated by ratings for 2008 and 2009 from the 2007 NTEP test. In this test, the turf quality of 'Latitude 36 Turf Bermudagrass' has been statistically equal to that of Tifway and Premier. These three varieties along with another OSU entry (OKC 1134), have had the highest quality ratings of all 31 entries at most locations (2008 NTEP Tables 1A&C, 2A&C, 3A&C, & 4A&C; 2009 NTEP Tables 1A&C, 2A&C, 3A&C, & 4A&C). The high turf quality of 'Latitude 36 Turf Bermudagrass' as indicated by NTEP data is supported by data from initial OSU testing indicating it to have turf quality equal to or better than other current industry standard bermudagrass varieties.

Cold tolerance and spring greenup: Freeze tolerance evaluations conducted at OSU provided T mid values eC, cultivars followed by the same letter are not significantly different in freeze tolerance at P:S 0.05) for 'Latitude 36 Turf Bermudagrass' (−8.4a), Midlawn (−8.3a), Tifway (−7.5b). The results indicated 'Latitude 36 Turf Bermudagrass' has a level of freeze tolerance on a par with that of Midlawn and superior to Tifway. Midlawn has been widely known as one of the most cold hardy turf bermudagrass varieties. Spring greenup ratings of Latitude 36 Turf Bermudagrass, 6.3 in 2008 and 6.2 in 2009, were statistically higher than or equal to that of Tifway (5.5 and 5.7), Premier (5.3 and 6.0), and Midlawn (5.3 and 4.3) (2008 NTEP Table 8C and 2009 NTEP Table tOC). Spring greenup ratings are a good indicator for winter hardiness of bermudagrass based on field evaluations. The level of winter hardiness of 'Latitude 36 Turf Bermudagrass' should allow it to be used in the transition zone environment with reduced risk of freeze injury relative to Tifway.

Genetic color: 'Latitude 36 Turf Bermudagrass' was rated statistically equal to Tifway and Premier, and superior to Midlawn in genetic color (2008 NTEP Table 7C and 2009 NTEP Table 9C). 'Latitude 36 Turf Bermudagrass' is lighter green in color than 'Patriot' bermudagrass. 'Latitude 36 Turf Bermudagrass' grown in the field with 100 lb N/ac applied in the summer had leaves of strong yellowish green color, rated as RHS143C, similar to Tifway, but less dark than Tifton 10, which was rated as RHS 144A. The leaf color was visually rated based on the color systems of Azalea Society of America (http://www.azaleas.org/index.pl/rhsmacfan3.html).

Leaf texture: 'Latitude 36 Turf Bermudagrass' has finer leaf texture than Tifway, Premier and Midlawn (2008 NTEP Table 9C and 2009 NTEP Table 11 C). Its stem diameter is about the same as Tifway and Premier.

Sod tensile strength: 'Latitude 36 Turf Bermudagrass' has provided excellent sod tensile equivalent to that of Tifway under testing conditions at Stillwater, Okla. (Han, 2009). Tifway has been a standard for sod tensile strength and handling quality for several decades. Sod tensile strength ($kg/dm^2$) for 'Latitude 36 Turf Bermudagrass' (185.6 in Yr 2004 and 162.7 in 2005) and for Tifway (161.3 in 2004 and 143.7 in 2005) were not statistically different (Han, 2009).

Sod density: Ratings in spring, summer and fall in multiple locations over both 2008 and 2009 indicated sod density of 'Latitude 36 Turf Bermudagrass' is slightly higher than or about equal to that of Tifway and Premier, and significantly higher than that of Midlawn (2008 NTEP Tables tOC, 11C, 12C; 2009 NTEP Tables 12C, 13C & 14C).

Seed head ratings: In 2008, 'Latitude 36 Turf Bermudagrass' had seedhead ratings better than or equal to Tifway, Premier and Midlawn in most locations, but produced more seedheads than Midlawn and Tifway in TX2 (2008 NTEP Tables 21C, 22C, 23C & 24C). In 2009, 'Latitude 36 Turf Bermudagrass' had seedhead ratings better than or equal to Tifway, Premier and Midlawn in all locations (2009 NTEP Tables 24C, 28C, 29C, 30C & 31 C).

Disease response: 'Latitude 36 Turf Bermudagrass' has demonstrated a high level of resistance to Large Patch disease (2009 NTEP 27C).

Insect response: No significant insect problems have been observed for 'Latitude 36 Turf Bermudagrass' except in FL1, where the mole cricket damage rating of 'Latitude 36 Turf Bermudagrass' was numerically lower than that of Tifway, Midlawn and Premier although the differences were not statistically significant (2009 NTEP Table 26C).

Salinity response: Grown under saline stress at Las Cruces, N. Mex., 'Latitude 36 Turf Bermudagrass' has demonstrated a high level of salinity tolerance, better than Midlawn, Premier and Tifway in 2008, better than Midlawn and Premier and equal to Tifway in 2009 (2008 NTEP Table 6C, 2009 NTEP Table 8C).

Traffic tolerance: Traffic tolerance ratings of 'Latitude 36 Turf Bermudagrass' were equal to that of Tifway and Premier, better than that of Midlawn at Arkansas test site 2 (AR2) and Florida test site 2 (FL2) (2009 NTEP Tables 5C, 6C). 'Latitude 36 Turf Bermudagrass' had traffic tolerance better than or equal to Tifway, Premier and Midlawn at North Carolina test site 1 (NC 1) (2009 NTEP Table 7C). 'Latitude 36 Turf Bermudagrass' under traffic stress tested in 2008 was lower in traffic tolerance than Tifway, equal to Premier, and superior to Midlawn in FL2 (2008 NTEP Table 5C).

Herbicide tolerance: OSU field experiments indicated the effects of various postemergence herbicides on the establishment rate of 'Latitude 36 Turf Bermudagrass' compared to OKC 1134, OKC 7018 and Tifway (Koh et ai., 2010). Herbicide treatments were as follows: 1) Untreated control, 2) MSMA at 2.2 kg ailha, 3) MSMA at 4.4 kg ailha, 4) Quinc10rac at 0.8 kg aelha, 5) Quinclorac at 1.6 kg aelha, 6) Metsulfuron at 0.025 kg ailha, and 7) Metsulfuron at 0.050 kg ailha. There was no negative effect on 'Latitude 36 Turf Bermudagrass' establishment rate when treated with the labeled rates of the herbicides. In addition, 'Latitude 36 Turf Bermudagrass' performed equal to Tifway and OKC 1134 and greater than OKC 7018 in herbicide tolerance ratings and reached 100% establishment at 8 weeks after planting.

Establishment: Establishment ratings of 'Latitude 36 Turf Bermudagrass' were better than that of Tifway, and equal to that of Premier and Midlawn at Stillwater, Okla. (OK1) and TX2 (2007 NTEP Tables 21C & 23C), equal to that of Premier, Tifway and Midlawn in AZ1, MS2, TN2 (2007 NTEP Tables 17C, 19C, 22C), was slower than that of Premier, equal to that of Midlawn, and higher than that of Tifway in LAI (2007 NTEP Table 18C), better than Midlawn and Tifway, and lower than that of Premier in NC2 (2007 NTEP Table 20C). 'Latitude 36 Turf Bermudagrass' had an establishment rate slightly slower than Premier and Tifway, but quicker than Midlawn in FL2 (2008 NTEP Table 28C), and slower than Premier and Tifway and equal to Midlawn in FL3 (2008 NTEP Table 29C).

Summary comparative performance: The major strengths of 'Latitude 36 Turf Bermudagrass' are its exceptional turf quality, fine texture, improved winter hardiness, high sod density, and very good sod tensile strength. The combined performance data indicate it has less risk of winter injury than Tifway, perhaps Premier, while providing higher or equal turf quality. Compared to Midlawn, its turf quality is much improved. 'Latitude 36 Turf Bermudagrass' is also better than Midlawn in sod tensile strength, a major consideration for sod growers.

We claim:

1. A turf bermudagrass plant substantially as described and illustrated in the specification herein.

* * * * *